United States Patent
Johnson et al.

(10) Patent No.: US 11,110,262 B2
(45) Date of Patent: Sep. 7, 2021

(54) PERCUTANEOUS SHEATHS FOR USE WITH PERCUTANEOUS VENTRICULAR ASSIST DEVICES

(71) Applicant: Synecor LLC, Chapel Hill, NC (US)

(72) Inventors: Kevin Johnson, Durham, NC (US); Richard S. Stack, Chapel Hill, NC (US); William L. Athas, Chapel Hill, NC (US)

(73) Assignee: SYNECOR, LLC, Durham, NC (US)

( * ) Notice: Subject to any disclaimer, the term of this patent is extended or adjusted under 35 U.S.C. 154(b) by 0 days.

(21) Appl. No.: 16/579,781

(22) Filed: Sep. 23, 2019

(65) Prior Publication Data

US 2021/0085848 A1    Mar. 25, 2021

(51) Int. Cl.
*A61M 60/148* (2021.01)
*A61M 60/857* (2021.01)
*A61M 60/892* (2021.01)

(52) U.S. Cl.
CPC ........ *A61M 60/148* (2021.01); *A61M 60/857* (2021.01); *A61M 60/892* (2021.01); *A61M 2209/04* (2013.01)

(58) Field of Classification Search
CPC .............. A61M 2209/04; A61M 1/122; A61M 1/1008; A61M 1/1087
See application file for complete search history.

(56) References Cited

U.S. PATENT DOCUMENTS

| | | | |
|---|---|---|---|
| 2011/0118766 A1* | 5/2011 | Reichenbach | .......... A61M 1/10 606/153 |
| 2014/0051908 A1* | 2/2014 | Khanal | ............... A61M 60/422 600/17 |

* cited by examiner

*Primary Examiner* — Carl H Layno
*Assistant Examiner* — Anh-Khoa N Dinh

(57) ABSTRACT

Percutaneous access sheaths used to provide access to the vasculature and heart for the introduction of percutaneous ventricular assist devices (pVADs), and to remain in place for the duration of pVAD use. The sheaths include actively closeable seals engageable to seal against the drive lines of the pVADs to minimize blood loss during pVAD use.

7 Claims, 10 Drawing Sheets

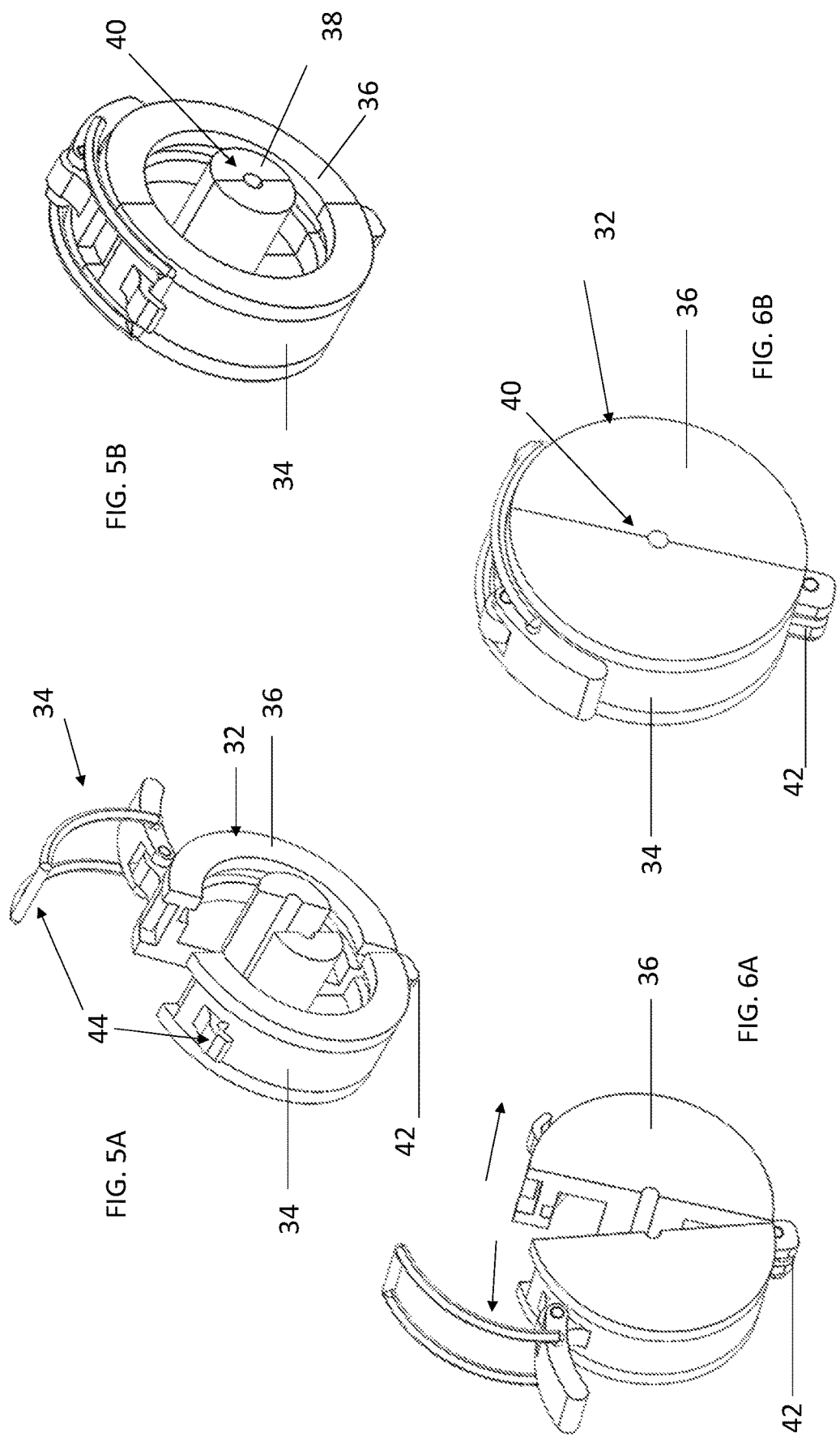

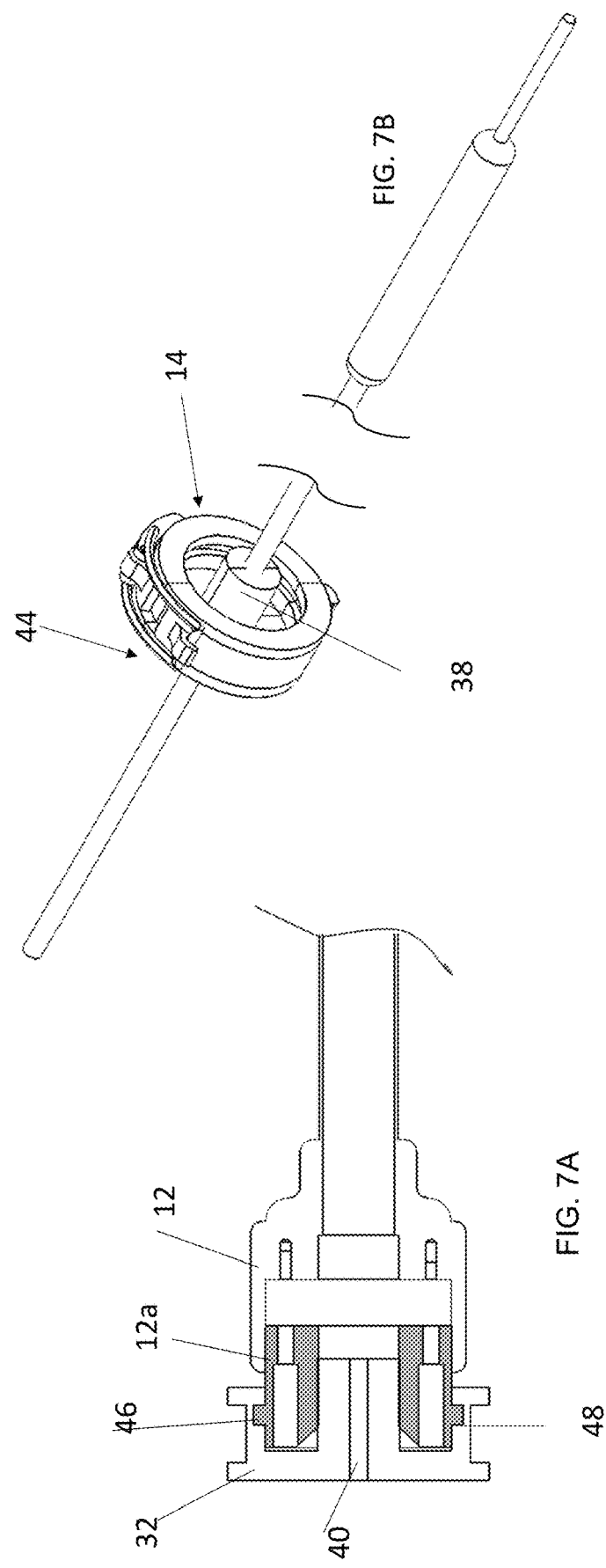

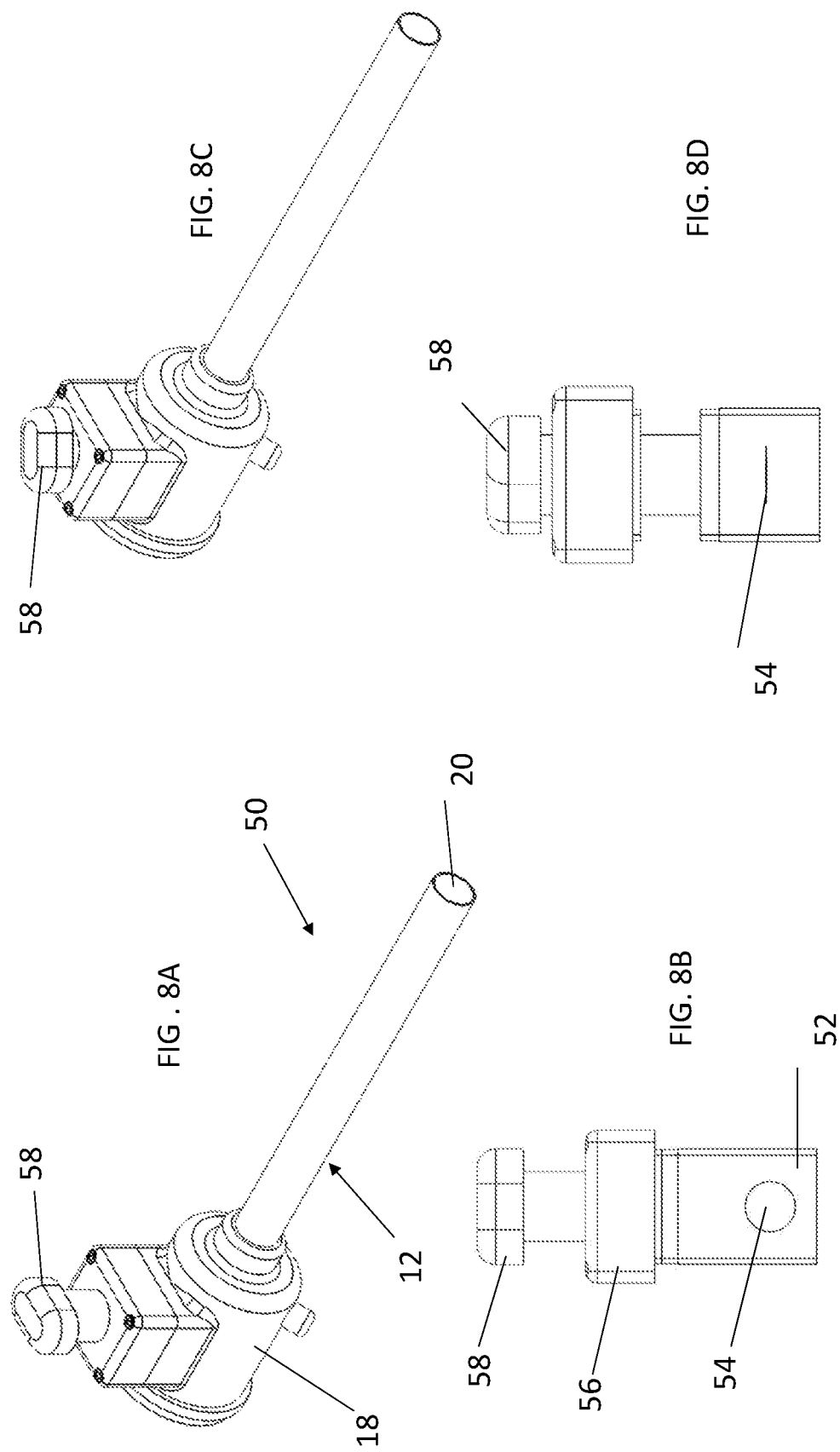

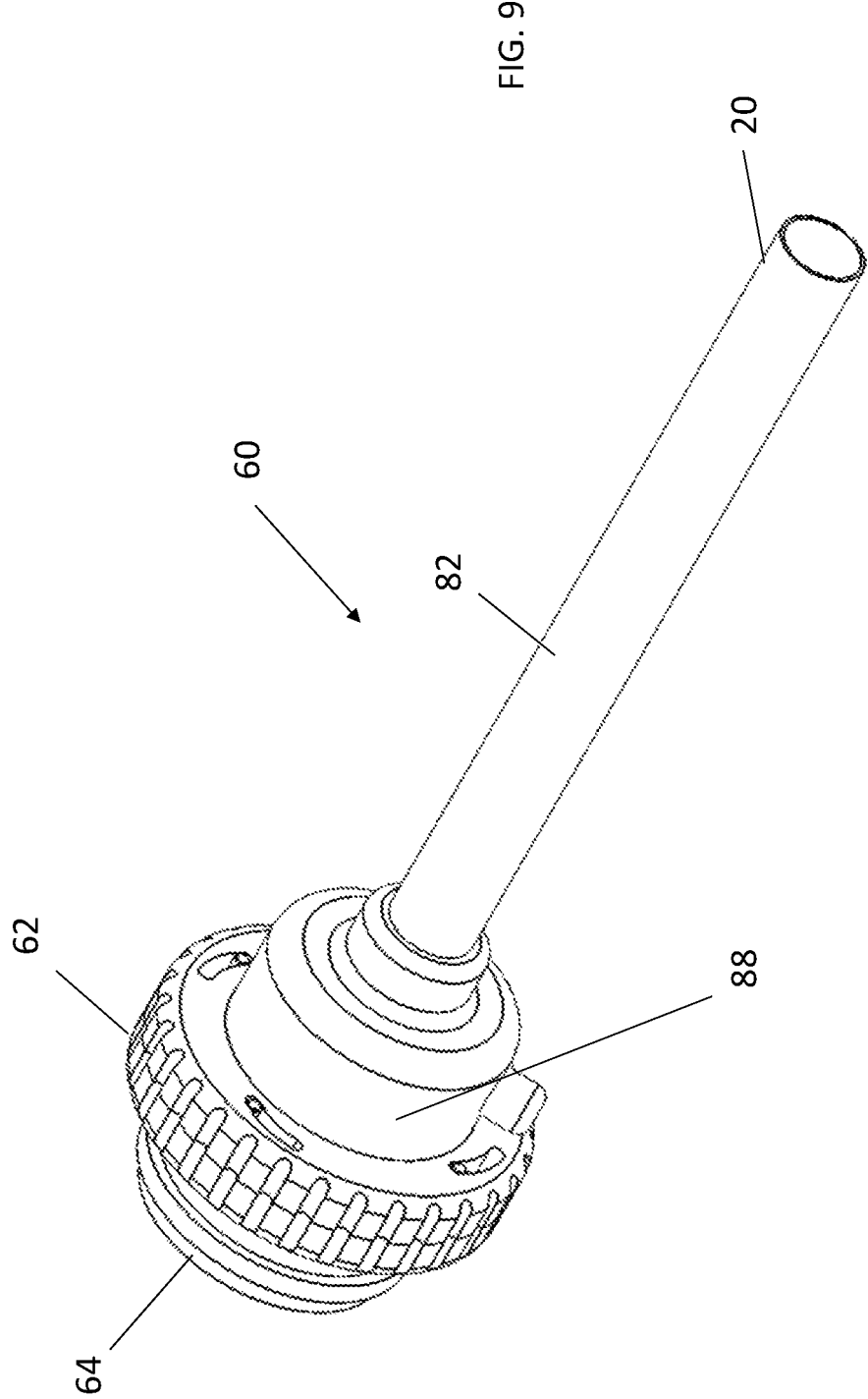

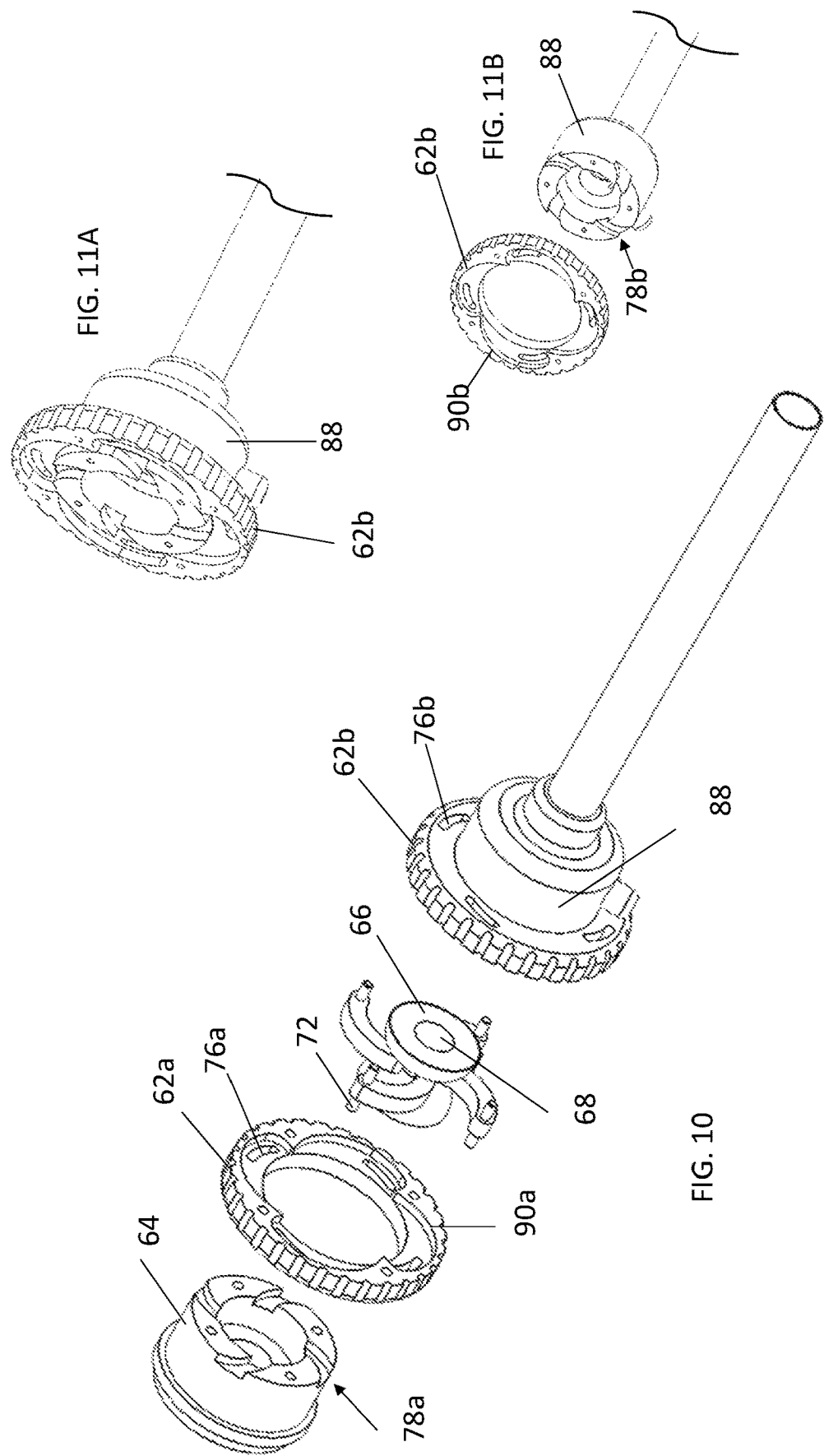

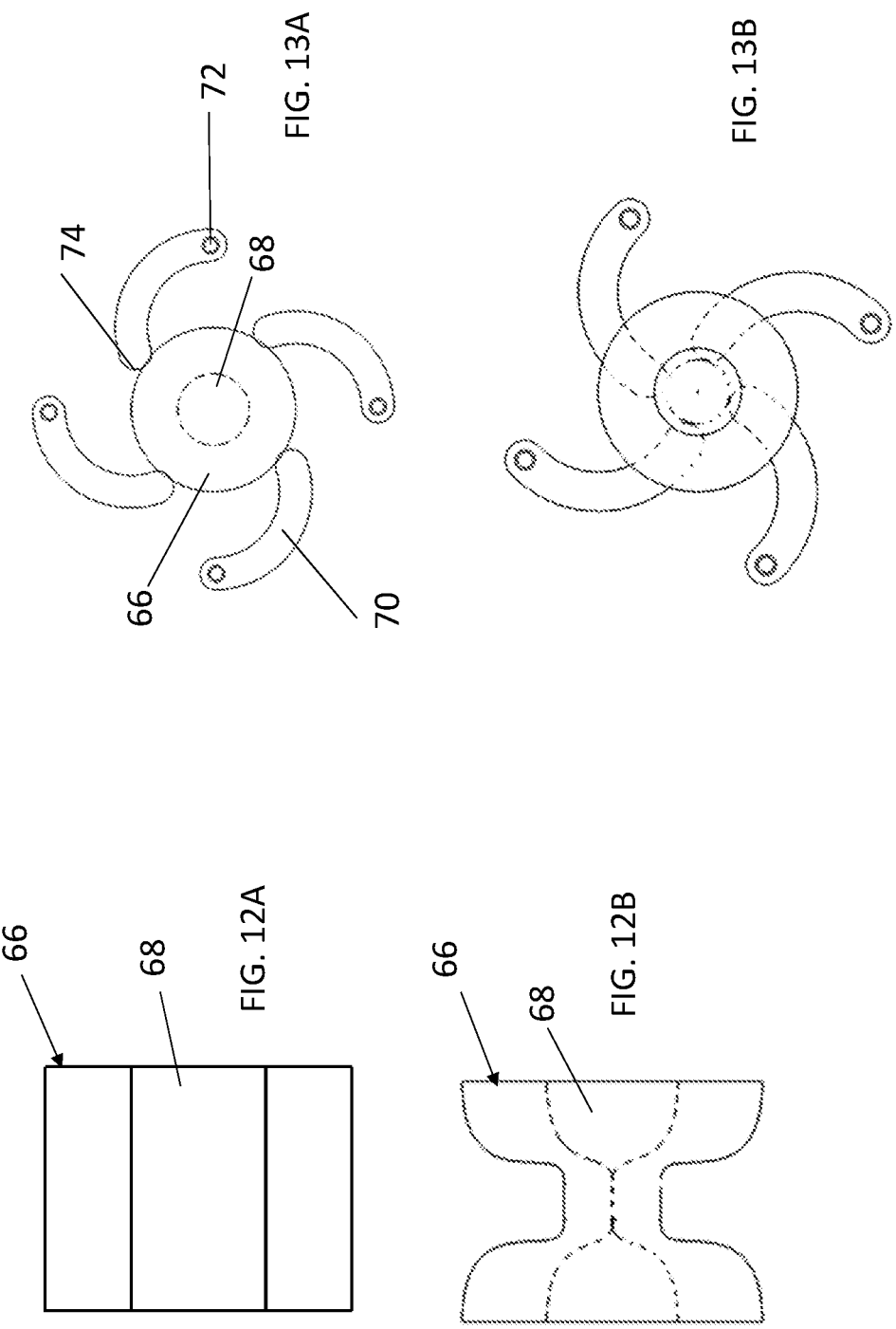

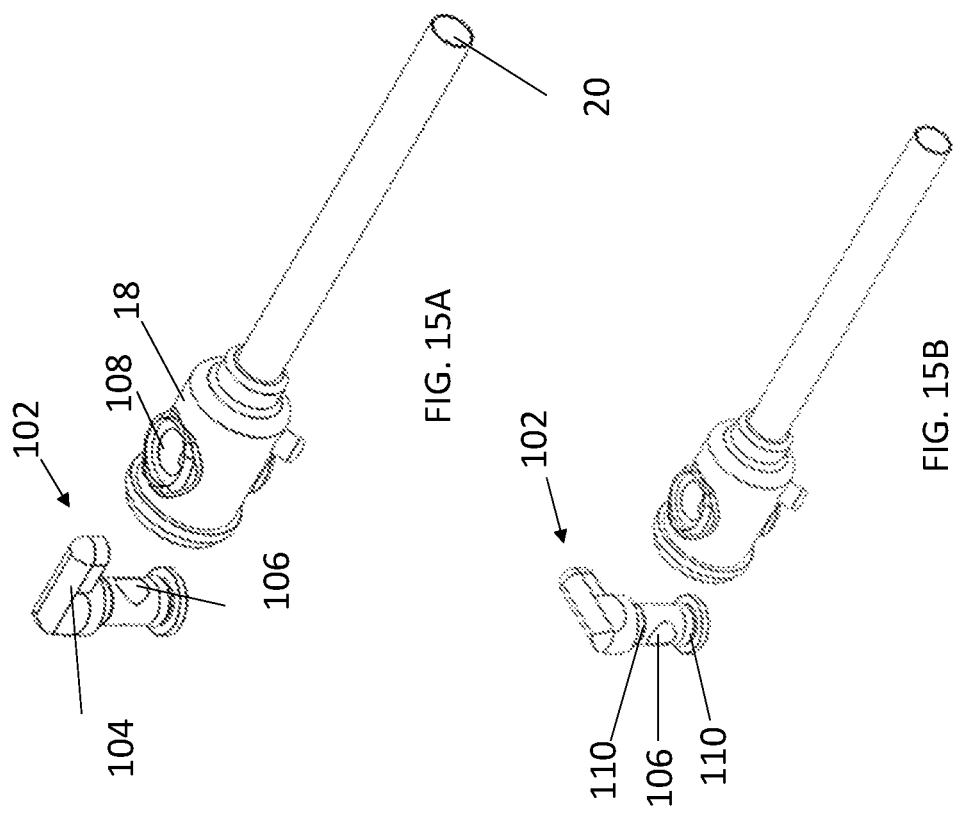
FIG. 15A
FIG. 15B
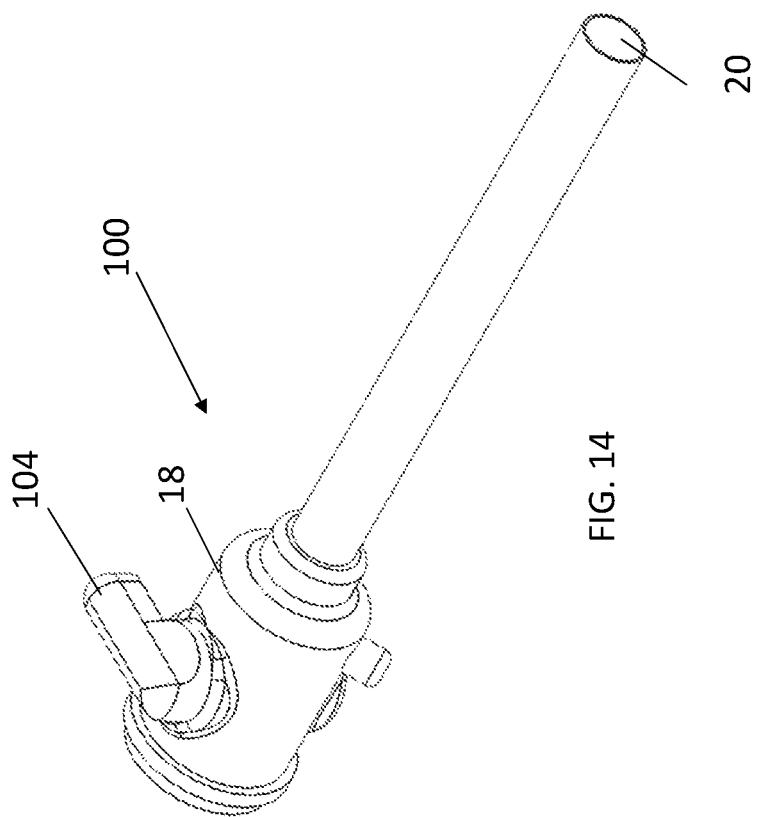
FIG. 14

PERCUTANEOUS SHEATHS FOR USE WITH PERCUTANEOUS VENTRICULAR ASSIST DEVICES

BACKGROUND

Percutaneous sheaths are tubular access devices commonly used to gain percutaneous access of the human vasculature. Co-pending U.S. application Ser. No. 16/578,375, entitled Systems and Methods for Transseptal Delivery of Percutaneous Ventricular Assist Devices and Other Non-Guidewire Based Transvascular Therapeutic Devices, filed 22 Sep. 2019 and incorporated herein by reference, describes a system and method for percutaneous delivery of a percutaneous ventricular assist device (pVAD) into the vascular. In one exemplary embodiment described in that application, percutaneous sheaths of various sizes are placed at four vascular access sites: right femoral artery (RFA-16 F sheath), the right femoral vein (RFV-11 F sheath), the left femoral artery (LFA-8 F sheath), the left femoral vein (LFV-11 F sheath), and the right subclavian vein (RSV-26 F Sheath). One of the sheaths, which in that application is the RSV sheath, serves a number of different functions having different requirements. It creates access to the vasculature and heart for instruments used in the delivery procedure, and for the pVAD device itself. It provides support within the vasculature for advancement of the pVAD device towards and into the right atrium. Finally, it is desirable to have that sheath remain in the vasculature as the conduit through which the drive line of the pVAD exits the body of the patient during the period of time in which the pVAD is in use.

The present application describes sheaths suitable for performing these functions. Preferred sheaths thus feature actively closable seals used to minimize blood loss by preventing fluid leakage around the drive line of the pVAD once it has been implanted, as well as elements that securely engage the sheath to the drive line to avoid unintended displacement of the pVAD within the patient's body. Some embodiments also include seals that seal against the shafts of any devices or instruments passed through them during the pVAD implantation process.

BRIEF DESCRIPTION OF THE DRAWINGS

FIG. 5A is a perspective view showing the distal face of the hinged seal, with the seal in the open position.

FIG. 5B is a perspective view showing the distal face of the hinged seal, with the seal in the closed position.

FIG. 6A is a perspective view showing the proximal face of the hinged seal, with the seal in the open position.

FIG. 6B is a perspective view showing the proximal face of the hinged seal, with the seal in the closed position.

FIG. 7A is a cross-sectional side view of the main body of the sheath and the seal halves. The baffle seal assembly and the locking element of the hinge seal are not shown for clarity. The proximal part of the main shaft is shown with shading.

FIG. 7B is a perspective view showing the hinged seal in the closed position to seal against the shaft of a pVAD device. For clarity, the main body of the sheath is not shown.

FIG. 8A is a perspective view of third embodiment of a sheath, with the open-close assembly in the open position.

FIG. 8B is a front elevation view of the open-close assembly of the sheath of FIG. 8A in the open position.

FIG. 8C is similar to FIG. 8A but shows the open-close assembly in the closed position.

FIG. 8D is a front elevation view of the open-close assembly of the sheath of FIG. 8A in the closed position.

FIG. 9 is a perspective view of a fourth embodiment of a sheath.

FIG. 10 is an exploded perspective view of the sheath of FIG. 9.

FIG. 11A is a perspective view showing the proximal face of the distal ring of the articulation knob housing and proximal housing of the sheath of FIG. 9.

FIG. 11B is similar to FIG. 11A but shows the ring and proximal housing separated.

FIG. 12A is a side elevation view of the seal of the sheath of FIG. 9 in the open position.

FIG. 12B is similar to FIG. 12A but shows the seal in the closed position.

FIG. 13A is a front elevation view showing the position of the pinch fingers relative to the seal when the sheath is in the open position.

FIG. 13B is a front elevation view showing the position of the pinch fingers relative to the seal when the sheath is in the closed position.

FIG. 14 is a perspective view of a second embodiment of a sheath.

FIG. 15A is similar to FIG. 14 but shows the stopcock assembly separated from the main body. In this figure, the stopcock assembly is in the opened position.

FIG. 15B is similar to FIG. 14 but shows the stopcock assembly separated from the main body. In this figure, the stopcock assembly is in the closed position.

DETAILED DESCRIPTION

First Embodiment

FIGS. 1 through 7B depict a first embodiment of a sheath 10. Sheath 10 is generally comprised of a rigid main body 12 and a removable hinged seal 14.

Figure 2:
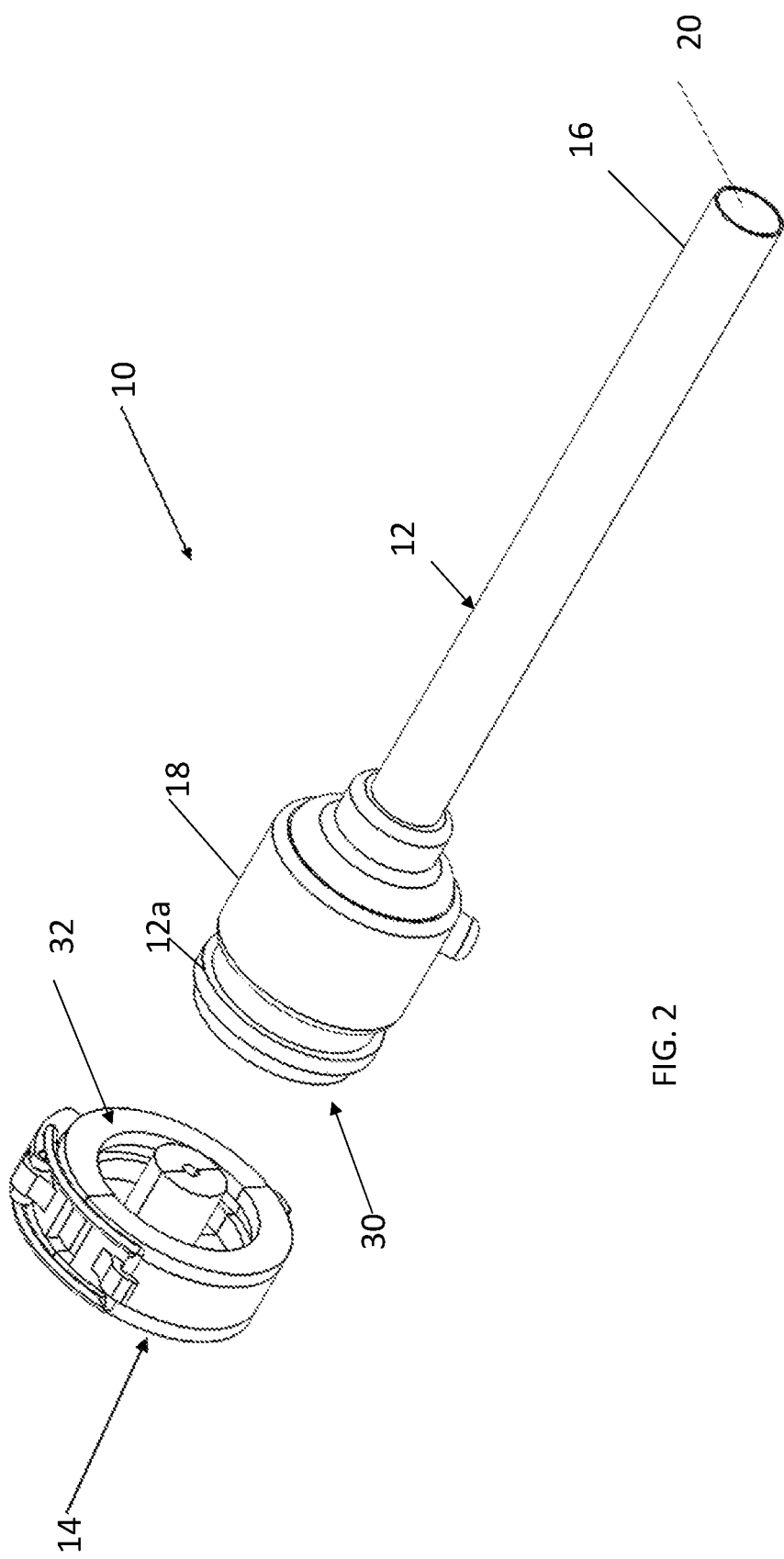
FIG. 2 is similar to FIG. 1, but shows the hinged seal separated from the main body.

Referring to FIG. 2, the main body 12 includes a shaft 16 and a proximal seal housing 18. In use the shaft 16 is positioned extending through a percutaneous incision and into a blood vessel such as the right subclavian vein, while the proximal seal housing 18 remains external to the incision. The proximal seal housing 18 preferably has a larger diameter than the shaft 16, as is commonly the case with sheaths, trocars, etc. A lumen 20 extends through the main body 12 from the proximal face of the seal housing 18 to the distal tip of the shaft 16. The main body 12 includes a proximal part 12a that includes an opening, giving access into the lumen 20.

The housing 18 houses one or more seals that will seal against the shafts of devices passed through the main body 12 during a percutaneous procedure. If the sheath 10 is used for percutaneous delivery of a pVAD, these seals seal against the devices used in the process of delivering the pVAD during the delivery process, and following implantation they seal against the drive line of the pVAD which remains extending through the sheath 10 between the external drive system for the pVAD and the pVAD itself. Various seal configurations are known in the art for use in vascular access devices and surgical trocars, and any type of seals suitable for sealing against an instrument shaft may be used in the seal housing for this purpose. The configuration illustrated in FIG. 3, incorporates a baffle seal assembly 22 comprised of two or more baffle seals 24 separated by spacers 26. A proximal cap 30 retains the baffle seal assembly 22 within the seal housing 18.

Figure 4A:
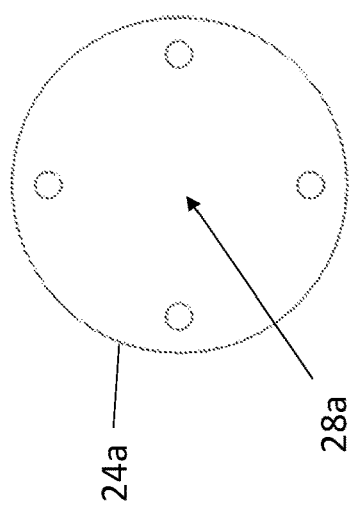
FIG. 4A is a first embodiment of a baffle seal.
Figure 4B:
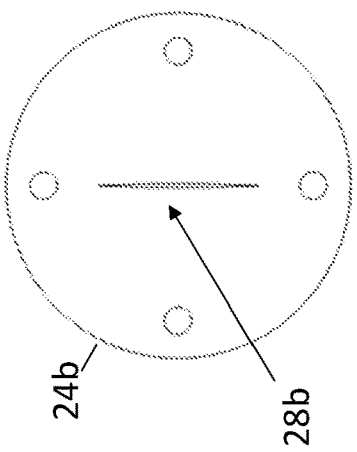
FIG. 4B is a second embodiment of a baffle seal.
Figure 3:
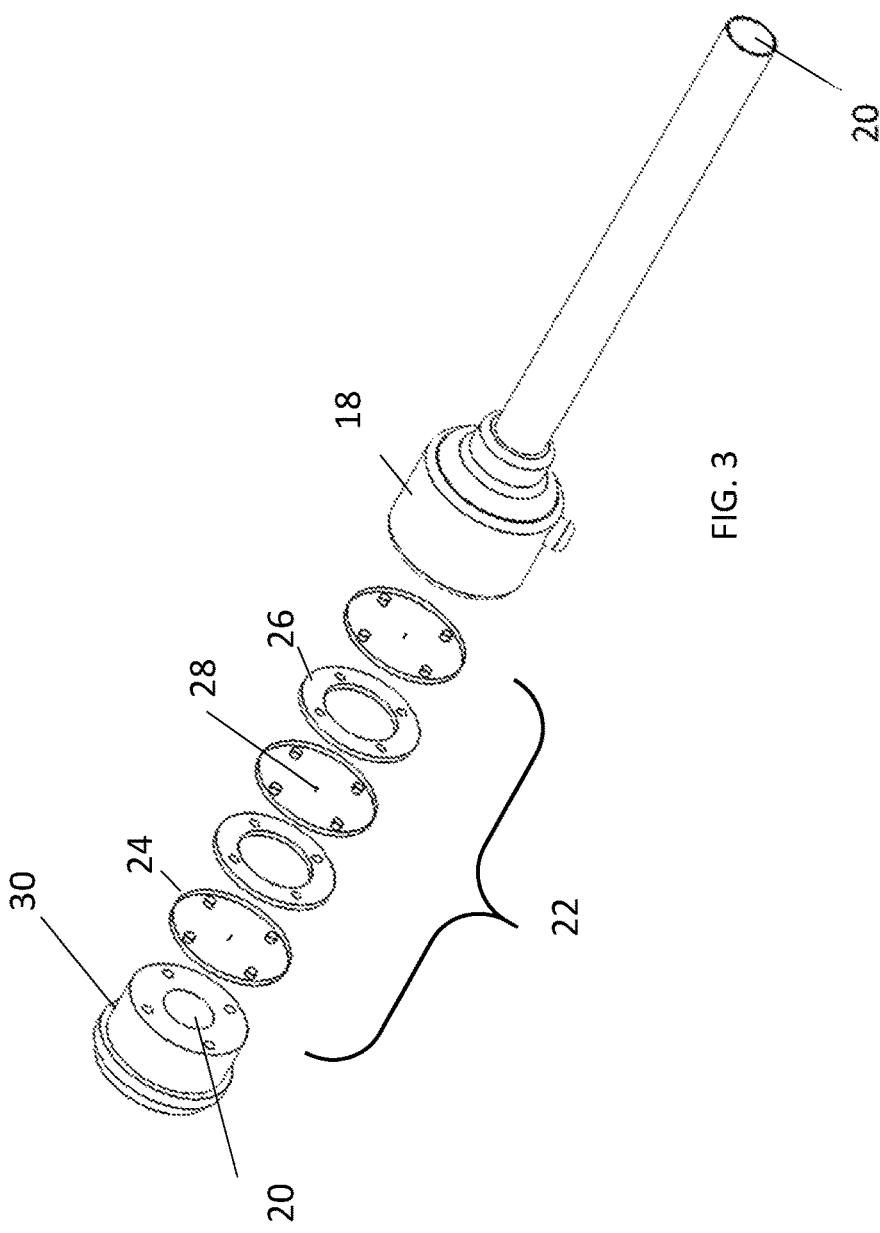
FIG. 3 is an exploded perspective view of the main body, showing the baffle seal assembly.

Each baffle seal 24 includes an opening 28 through which a device or instrument is passed during use. The shape of the opening and the elastomeric sealing material for the baffle seal are chosen so that the opening remains sealed when no instrument passes through it, and so that the material surrounding the opening seals against an instrument that extends through it. Suitable materials for the seal include elastomeric materials such as silicone. Two exemplary shapes for the opening are shown in FIGS. 4A and 4B, with the seal 24a of FIG. 4A including a pinhole 28a, and the seal 24b of FIG. 4B including a slit 28b. When the slit shape of FIG. 4B is used, each baffle seal in the baffle seal assembly may be arranged with its slit rotated by some degree (e.g. 90°) relative to the slit of the adjacent baffle seals. Other opening shapes may alternatively be used.

Turning again to FIG. 2, the hinged seal 14 is designed to removably connect to the proximal cap 30 of the main body 12. As will be explained in greater detail below, when the sheath is used at an access site through which a pVAD is delivered and tethered to its drive unit, the hinged seal 14 is not present on the main body 12 for the steps of introducing the pVAD through the sheath 10 into the vasculature. However, once the pVAD is positioned at its target site, the hinged seal 14 is positioned with the drive line of the pVAD extending through it and with the hinged seal 14 coupled to the proximal cap 30 of the main body 12. In this way, the hinged seal 14 is used to provide additional sealing around the shaft of the drive line (which is also in sealing contact with the baffle seals), but it helps to retain the drive line in a fixed longitudinal position at the incision site to prevent unintended movement of the pVAD within the heart.

Referring to FIGS. 5A through 6B, the hinged seal 14 includes an actively closable seal 32 and a locking element 34 for locking the seal 32 in the closed position. The seal 32 may take a variety of forms, but in the illustrated embodiment it includes a pair of seal halves 36. The regions of the seal halves 36 surrounding the longitudinal axis of the seal 32 together form an extension 38 having a sealing lumen 40. When the seal halves are in the closed position shown in FIGS. 5B and 6B, the lumen 40 and extension 38 are formed. The seal halves are moved to the open position by pivoting the seal halves relative to one another in the direction indicated by the arrows in FIG. 6A, with opposed edges of the seal halves (which in FIGS. 5A and 6A are the lower edges) hinging about one another. The seal 32 can be made of silicone or an alternative elastomeric material.

The illustrated locking element 34 is a rigid band circumferentially positioned around the seal halves 36. This band includes a pair of band halves joined by a hinge 42. Movement of the band halves relative to one another about the hinge moves the band between the closed position shown in FIGS. 5B and 6B, and the open position shown in FIGS. 5A and 6A, in which the ends of the band halves are pivoted away from one another. A fastener such as latch 44 (FIG. 5A) is engageable by a user to retain the band in a closed configuration, and to thus place the seal 32 in the closed position.

Figure 1:
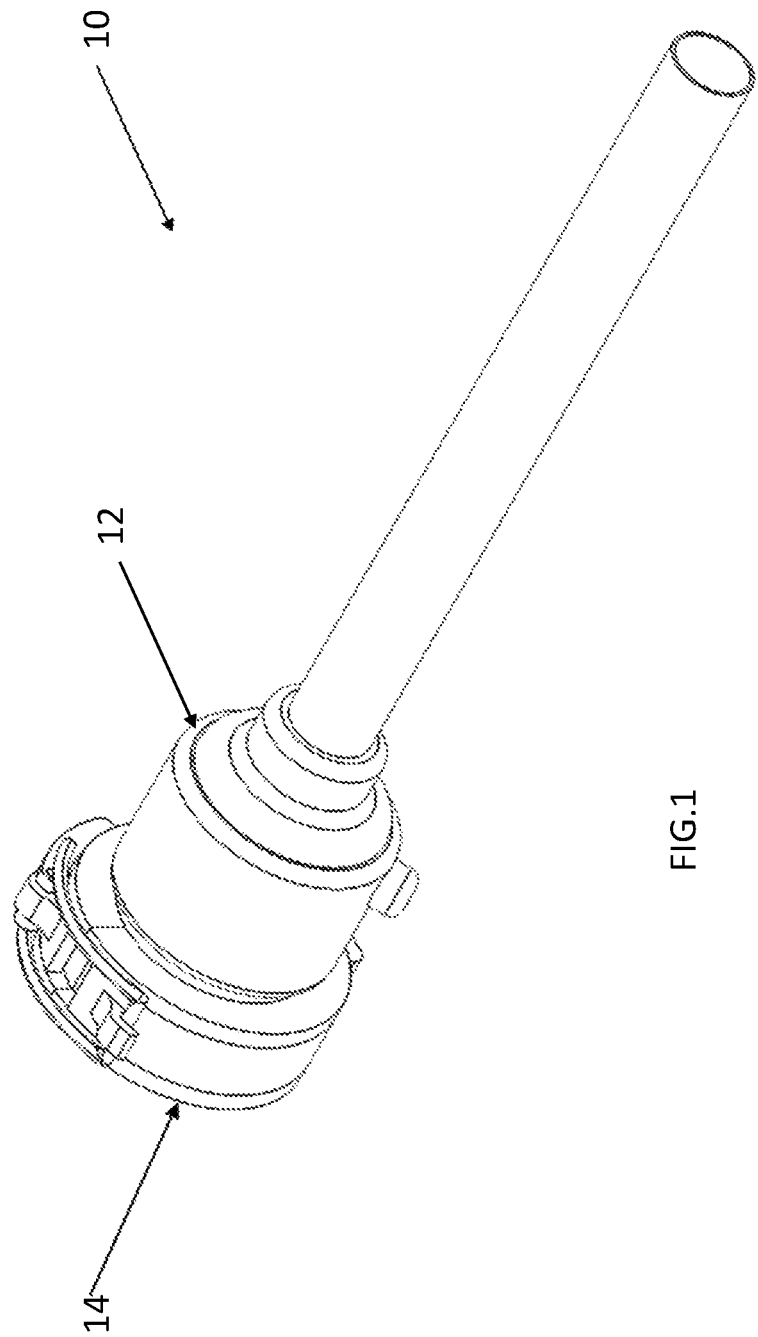
FIG. 1 is a perspective view of a first embodiment of a sheath, showing the hinged seal in place and in the closed position.

Referring to FIG. 7A, when the seal 32 is mounted to the main body 12 of the sheath in the position shown in FIG. 1, the extension 38 is inserted into the opening in the proximal part 12a (shown shaded) of the main body 12. Within the proximal part 12a are features that squeeze the extension 38 of the seal 32 radially inwardly, enhancing the sealing contact between the walls lining the lumen 40 of the extension and a device extending through that lumen 40. Those features might include walls that funnel or taper inwardly from a proximal to distal direction, or an opening in the lumen that is slightly smaller in diameter than the outer diameter of the extension 36, or both (as shown in FIG. 7B). To promote peripheral sealing around the circumference of the seal 32, a circumferential ridge 46 around the proximal part 12a is received into a circumferential groove 48 around the seal 32 as shown. In alternate embodiments, ridge 46 might be replaced with a groove that receives a corresponding ridge of the seal 32. The lumen 40 allows for the seal 32 to be positioned around a device passing through the sheath and to seal off when it is closed and inserted into the proximal part of the main body 12a.

Use of the first embodiment will next be described in the context of treatment of a patient using a pVAD. The main body 12 is positioned in a percutaneous incision to give access to the vasculature for devices used in the pVAD implantation process. When passed into the lumen 20, those devices extend through the openings 28 in the baffle seals 24 so the surrounding edges of the openings seal against the devices, minimizing blood loss. At the end of the implantation procedure, the pVAD device is situated with its pump in the heart and its drive line extending out of the heart, through the vasculature and out of the body via the main sheath 12. It is at this point that the hinged seal 14 is placed on the drive line and the main sheath. To do this, the user positions the hinged seal 14 in the opened position (as in FIG. 5A) so that the lumen 40 that will be formed when the seal is closed is aligned with the shaft of the drive line. The hinged seal 14 is closed on the shaft to seal the shaft within the lumen 40 as shown in FIG. 7B. The hinged seal 14 is positioned on the main body 12 as described in the previous paragraph, with the extension 38 being inserted into the proximal part 12a of the main body to squeeze the walls surrounding lumen 40 against the shaft of the drive line, and with the circumferential rail 46 around the proximal part 12a being seated in the circumferential groove 48 around the seal 32. In this way, the seal 32 creates a seal against the drive line in order minimize blood loss, and it helps to securely engage the drive line to prevent unintended displacement of the pVAD within the patient's body. The latch 44 seal is tightened to fully engage the seal and prevent it from separating from the hub.

Second Embodiment

FIGS. 8A-8D show a second embodiment of a sheath 50. This embodiment uses a seal 52 having a pre-formed seal lumen 54 that allows for passage of instruments through it, but that may be subjected to lateral compression to collapse it in order to seal it against fluid loss.

Seal 52 is positioned in the housing 18 of the main shaft 12, with its lumen 54 aligned with the main shaft's lumen 20. A compression plate 56 contacts the seal 52 within the housing, and a push rod 58 is positioned to drive the compression plate 56 against the seal 52. When the push rod 58 is depressed by a user, the compression plate 56 compresses the seal, causing the lumen 54 of the seal to move from the open position shown in FIG. 8B to the closed position shown in FIG. 8D. A locking mechanism (not shown) may be included to maintain compression so the seal remains in the closed position until actively released by the user. In one example, rotation of the plunger in a first direction by a predetermined amount (e.g. 45 degrees) locks the plunger in the depressed position, while rotating the plunger in the opposition direction unlocks the plunger and causes it to return to its elevated position under action of the expanding seal 52.

The main shaft 12 or housing 18 may include additional seals such as baffle seals of the type described in connection with the first embodiment.

Sheath 50 is optimally used as an alternative to the main sheath body 12 shown in FIG. 1. When used in this manner, the sheath 50 would provide access for instruments during a pVAD implantation procedure. During such use, devices used during the procedure extend through the lumen 54 of the seal 52 as well as through any such additional seals. The compression plate 56 is advanced to close the seal when no devices are passing through the lumen sheath. It also may be advanced to close the seal around the shafts of instruments extending through the sheath.

After the pVAD is positioned in the left ventricle, the hinged seal 32 described with respect to FIGS. 5A-6B would then be mounted to the proximal housing 18 and used to seal against the drive line of the implanted pVAD in the manner described with respect to the first embodiment.

Alternatively, instead of using the hinged seal, the seal 52 itself may be used to seal against the drive line. In this example, once the pVAD is positioned in the left ventricle, the push rod 58 is advanced to close the seal 52 against the shaft of the drive line, providing enhanced sealing for the period during which the pVAD is in place, and also restraining the drive line against unintended displacement relative to the percutaneous access site.

Third Embodiment

FIGS. 9 through 13B show a third embodiment of a sheath 60 incorporating an actively closeable seal. Sheath 60 includes a rotatable knob housing 62 concentrically positioned relative to the longitudinal axis of the sheath 60. A proximal cap retains the knob housing on the proximal housing 88 of the sheath 60. This proximal cap 64 has an opening on its proximal face, allowing access through the knob housing 62 into the lumen 20 of the sheath.

As best seen in the exploded view of FIG. 10, the rotatable knob housing 62 includes first and second rings 62a, 62b, each having a central opening. The proximal cap 64 extends through the openings in the rings and is fixed to the main body 82 of the sheath at the proximal housing 88. This connection retains the rings 62a, 62b on the main body 82 but allows rotation of the rings 62a, 62b relative to the main body 82.

A seal 66 is disposed within the volume enclosed by the proximal housing 88 and the proximal cap 64. The seal is formed of elastomeric material such as silicone and may have a cylindrical shape or an alternate shape. The seal includes a seal lumen 68 oriented along the pathway between the opening of the sheath and the lumen 20, and preferably aligned with its longitudinal axis along the longitudinal axis of the lumen 20.

The sheath further includes at least one compression member positioned to push against the exterior of the seal's circumferential sidewall in a direction towards the lumen 68 (e.g. in a lateral direction, which may be a direction transverse to the longitudinal axis of the lumen 68) in order to pinch the lumen closed. In this particular embodiment, four such compression members are shown, in the form of pivotable arcuate fingers 70. As most easily understood from FIGS. 13A and 13B, each such finger 70 includes a first end pivotable about a pin 72, and a second, free, end 74 pivotable into contact with the sidewall of the seal. When the lumen 68 is in the open position, the fingers are pivoted relative to the pins 72 to the position shown in FIG. 13A, positioning the free ends at or wider than the natural (uncompressed) outer circumference of the seal. To close the lumen 68, the fingers are pivoted about the pins 72 to the position shown in FIG. 13B, pushing the circumferential wall of the seal radially inwardly towards the longitudinal axis, thus pushing the wall into the lumen and closing the lumen. The fingers are preferably positioned relative to the seal so that the resulting pinch points are laterally aligned relative to the seal, as shown in FIG. 12B. This insures that the regions of wall material making ingress into the lumen make lateral contact with one another to form the seal. Note that while pivotable fingers are shown, other embodiments may use fingers that move linearly towards/away from the lumen such as, for example, fingers that advanced radially inwardly against the wall of the seal from multiple directions to close the lumen 68.

Referring again to FIG. 10, each pin 72 has a first end that slides within camming slot 76a in the ring 62a and a second end that slides within the camming slot 76b in the ring 62b. When the sheath is assembled, the fingers 70 are disposed between the rings 62, 62b and seated in arcuate channels 78a, 78b of the proximal cap 64 (FIG. 10) and the housing 88 (FIG. 11B), respectively. Each of these channels and corresponding contoured walls 90a, 90b on the rings 62a, 62b serve as guides for the travel of each arcuate finger 72 as it moves between the open and closed positions. When the knob 62 is rotated in a first direction, the camming slots 76a, 76b of the knob's rings 62a, 62b simultaneously push the pins 72 in a first direction, causing rotation of the fingers 70 to the closed position. Rotation of the knob 62 in the second, opposite direction, causes the camming slots to push the pin in the second, opposite direction, causing rotation of the fingers 70 to the open position.

The main shaft 82 or housing 88 may include additional seals such as baffle seals of the type described in connection with the first embodiment.

During use, devices used during the procedure extend through the lumen 68 of the seal 66 as well as through any such additional seals. As with the first embodiments, the additional seals would provide sealing around devices used during the procedure. Alternatively, or additionally, the lumen 68 in its open position may be relied on to provide some sealing around those devices. Once the pVAD is positioned, knob 62 is rotated to close the seal 66 against the shaft of the drive line by causing the fingers to radially compress the seal 66, providing enhanced sealing for the period during which the pVAD is in place, and also restraining the drive line against unintended displacement relative to the percutaneous access site. Note that this design allows for sealing against devices of varying diameters, since the knob can be turned by a small degree to close the seal a small amount (for a larger diameter instrument), and by a larger degree to close the seal by a larger amount or to fully close the seal. To release the seal from the device, the ring is turned in the opposite direction, causing the fingers to move radially outwardly, thus allowing the seal to open.

Fourth Embodiment

A fourth embodiment of a sheath 100 is shown in FIG. 4. This sheath is optimally used as an alternative to the main sheath body 12 shown in FIG. 1. In other words, the sheath 100 would provide access for instruments during a pVAD implantation procedure. Afterwards, the hinged seal 32 described with respect to FIGS. 5A-6B would be used to seal against the drive line of the implanted pVAD.

Sheath includes a stopcock body 102 having a lever 104 and a throughhole 106 positionable in alignment with the lumen 20 of the sheath 100. The stopcock body 102 is rotatably positioned within an opening 108 in proximal housing 18 of the sheath 100. O-ring seals 110 may be positioned to prevent fluid loss between the stopcock body and the edges of the surrounding opening. Alternatively, the stopcock body 102 may be formed of a seal material such as silicone, with the lever 104 attached to the seal body. The stopcock body 102 is manually rotatable between open and closed positions. In the open position, the opening 106 is oriented as depicted in FIG. 15A, in alignment with the lumen 20, so that instruments can be introduced into the proximal opening on the proximal housing 18 and passed through the lumen. In the closed position, the opening 106 is oriented offset from the lumen 20 as shown in FIG. 15B, preventing escape of fluids from the proximal opening of the sheath 100.

We claim:

1. A percutaneous access sheath comprising:
    an elongate tubular sheath having a sheath lumen and proximal and distal openings fluidly coupled to the sheath lumen;
    a seal having a seal lumen; and
    at least one compression member advanceable against a wall of the seal to push a portion of the wall into the lumen to move the seal lumen to a sealing position, wherein the at least one compression member includes a plurality of fingers pivotable to push at least partially opposed portions of the wall into the seal lumen; and an actuator moveable to simultaneously pivot the plurality of fingers to move the seal lumen to the sealing position.

2. The sheath of claim 1 wherein the actuator is a rotatable knob.

3. The sheath of claim 1, wherein the actuator is operatively associated with the fingers to cause the fingers to simultaneously move the portions into the seal lumen.

4. A method of using a percutaneous sheath, comprising:
    providing a percutaneous sheath having a sheath lumen and proximal and distal openings fluidly coupled to the sheath lumen, and a seal having a seal lumen; and
    advancing at least one compression member against a wall of the seal to push a portion of the wall into the lumen to move the seal lumen to a sealing position, wherein advancing the at least one compression member includes moving an actuator to simultaneously pivot a plurality of fingers to push at least partially opposed portions of the wall into the seal lumen.

5. The method of claim 4 wherein moving the actuator comprises rotating a rotatable knob to simultaneously pivot the plurality of fingers to move the seal lumen to the sealing position.

6. The method of claim 4, wherein the seal lumen includes a longitudinal axis and wherein advancing the at least one compression member includes advancing the at least one compression member in a direction towards, and transverse to, the longitudinal axis.

7. The method of claim 4, further including extending an instrument through the proximal and distal openings, the sheath lumen and the seal lumen, wherein advancing the compression member causes the seal to create sealing around the instrument to prevent fluids from passing around the instrument from within the sheath through the proximal opening.

* * * * *